(12) United States Patent
Noordam

(10) Patent No.: US 9,115,379 B2
(45) Date of Patent: Aug. 25, 2015

(54) PROCESS FOR THE PRODUCTION OF A COMPOSITION CONTAINING 5'-RIBONUCLEOTIDES

(75) Inventor: Bertus Noordam, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 56 days.

(21) Appl. No.: 13/984,705

(22) PCT Filed: Feb. 15, 2012

(86) PCT No.: PCT/EP2012/052545
§ 371 (c)(1),
(2), (4) Date: Aug. 9, 2013

(87) PCT Pub. No.: WO2012/110533
PCT Pub. Date: Aug. 23, 2012

(65) Prior Publication Data
US 2013/0316405 A1    Nov. 28, 2013

Related U.S. Application Data

(60) Provisional application No. 61/443,900, filed on Feb. 17, 2011.

(30) Foreign Application Priority Data

Feb. 17, 2011  (EP) ..................................... 11154867

(51) Int. Cl.
*C12P 19/30* (2006.01)
*A23L 1/229* (2006.01)
*A23L 1/30* (2006.01)

(52) U.S. Cl.
CPC ................. *C12P 19/30* (2013.01); *A23L 1/229* (2013.01); *A23L 1/3018* (2013.01)

(58) Field of Classification Search
USPC ............. 426/62, 650, 655, 532; 435/89, 91.1, 435/91.3, 259, 270, 6.1, 29, 306.1; 536/25.41, 127; 424/400; 504/117
See application file for complete search history.

(56) References Cited

U.S. PATENT DOCUMENTS

| 7,968,705 B2 | 6/2011 | Noordam et al. |
| 8,084,068 B2 | 12/2011 | Noordam et al. |
| 2006/0078972 A1 | 4/2006 | Noordam et al. |
| 2009/0148559 A1 | 6/2009 | Noordam et al. |

FOREIGN PATENT DOCUMENTS

| WO | 2004067758 A2 | 8/2004 |
| WO | 2005067734 A2 | 7/2005 |

OTHER PUBLICATIONS

International Search Report for PCT/EP2012/052454 Mailed Feb. 22, 2012.

*Primary Examiner* — Jane Zara
(74) *Attorney, Agent, or Firm* — Miles & Stockbridge

(57) ABSTRACT

The present invention describes a process comprising a) subjecting a microorganism to autolysis under conditions at which a substantial part of the RNA remains in a form degradable into 5'-ribonucleotides; b) subjecting the autolysate to solid/liquid separation and recovering the RNA-containing cell wall fraction; and c) converting the RNA in the recovered RNA-containing cell wall fraction into 5'-ribonucleotides, whereby the solid/liquid separation in step b) is done at a pH of lower than 5.1. Said process is simple and allows for the production of a very pure composition of 5'-ribonucleotides. It also allows for the production of a very clear yeast extract.

5 Claims, No Drawings

PROCESS FOR THE PRODUCTION OF A COMPOSITION CONTAINING 5'-RIBONUCLEOTIDES

FIELD OF THE INVENTION

The present invention relates to a process to produce a composition containing 5'-ribonucleotides.

BACKGROUND OF THE INVENTION

Compositions comprising 5'-ribonucleotides are known for their flavour enhancing properties. They are capable of enhancing the savoury and delicious taste in certain types of food. This phenomenon is described as 'mouthfeel' or umami.

The 5'-ribonucleotides are derived from RNA, usually from microorganisms such as yeast. WO2005067734 discloses a process to produce a composition comprising 5'-ribonucleotides where the process comprises subjecting a microorganism to autolysis under conditions at which a substantial part of the RNA remains in a form degradable into 5'-ribonucleotides, then subjecting the autolysate to solid/liquid separation and recovering the RNA-containing cell wall fraction and finally converting the RNA in the recovered RNA-containing cell wall fraction into 5'-ribonucleotides.

Autolytic extracts of microorganisms such as autolytic yeast extracts are concentrates of the soluble materials obtained from the microorganism (e.g. the yeast) after disruption of the cells and digestion (lysis) of the polymeric material (protein, carbohydrates, lipids, nucleic acids). The active microbial (e.g. yeast) enzymes released in the medium after cell disruption contribute to the lysis. These types of extracts are rich in amino acids and generally do not comprise 5'-ribonucleotides because during the autolytic process the native RNA is decomposed or modified in a form which is not degradable into 5'-ribonucleotides. In particular autolytic yeast extracts are used in the food industry as basic taste providers. The amino acids present in the yeast extract add a bouillon-type, brothy taste to the food.

Hydrolytic extracts of microorganisms, on the other hand, are concentrates of the soluble materials obtained after disruption of the cells, digestion (lysis) and addition of proteases and/or peptidases and especially nucleases to the suspension of the microorganism during lysis. The native microbial enzymes are inactivated prior to the lysis. During this process, 5'-ribonucleotides of guanine (5'-guanine mono phosphate; 5'-GMP), uracil (5'-uracil mono phosphate; 5'-UMP), cytosine (5'-cytosine mono phosphate; 5'-CMP) and adenine (5'-adenine mono phosphate; 5'-AMP) are formed. When adenylic deaminase is added to the mixture, 5'-AMP is transformed into 5'-inosine mono phosphate (5'-IMP).

Hydrolytic yeast extracts obtained by this method are rich in 5'-ribonucleotides, especially rich in 5'-GMP and 5'-IMP. Often yeast extracts are also rich in mono sodium glutamate (MSG). 5'-IMP, 5'-GMP and MSG are known for their flavour enhancing properties. They are capable of enhancing the savoury and delicious taste in certain types of food. This phenomenon is described as 'mouthfeel' or umami. Yeast extracts rich in 5'-ribonucleotides and, optionally, rich in MSG, are usually added to soups, sauces, marinades and flavour seasonings. Yeast extracts rich in 5'-ribonucleotides are preferably produced using yeast strains with a high RNA content and/or by partial extraction of the cell content.

A problem of the process disclosed in WO2005067734 is that the amount of 5'-ribonucleotides in the composition is too low and that due to the presence of amino acids and short peptides and of others yeast components, they are not very suitable for applications which require cleanliness of taste.

It is an object of the present invention to provide a process to produce compositions rich in 5'-ribonucleotides which are clean in taste, which process is simple and stable, i.e. which yields a constant high level of 5'-ribonucleotides. It is a further object to provide a process to produce yeast extract with little turbidity.

DETAILED DESCRIPTION OF THE INVENTION

In a first aspect the present invention provides a process to produce a composition containing 5'-ribonucleotides comprising: a) subjecting a microorganism to autolysis under conditions at which a substantial part of the RNA remains in a form degradable into 5'-ribonucleotides; b) subjecting the autolysate to solid/liquid separation and recovering the RNA-containing cell wall fraction and c) converting the RNA in the recovered RNA-containing cell wall fraction into 5'-ribonucleotides, whereby the solid/liquid separation in step b) is done at a pH of lower than 5.1 and higher than 1.0.

With the term "5'-ribonucleotides" it is herewith intended a mixture of 5'-GMP, 5'-CMP, 5'-UMP and further 5'-AMP and/or 5'-IMP, wherein said 5'-AMP may be either partially or completely converted into 5'-IMP. The term "5'-ribonucleotide(s)" encompasses the free 5'-ribonucleotide as well as a salt thereof.

In the context of the present invention autolysis of a microorganism is defined as a process wherein degradation of the microbial cells and of the polymeric microbial material is at least partially effected by active native microbial enzymes released in the medium after (partially) damaging and/or disrupting the microbial cell wall.

Any microorganism can be used as natural source of RNA in the process of the invention. Bacterial and fungal microorganisms are preferred, such as those which are suitable for food and feed applications. Preferred microorganisms are those that have the status of being food-grade and that can be safely applied in food for human consumption. Bacterial or fungal strains with a high RNA content (i.e. with an RNA content of typically 6-15%) enable the production of compositions with a high amount of 5'-ribonucleotides. However an advantage of the process of the invention is that also bacterial or fungal strains with a relatively low RNA content can be used. These strains can be advantageously used for the preparation of compositions containing a higher 5'-ribonucleotide content than would be expected on basis of the RNA content of the starting strain.

Examples of preferred microorganisms include filamentous fungi such as *Trichoderma* or *Aspergillus*, and yeasts such as *Saccharomyces*, *Kluyveromyces* and *Candida*. Strains belonging to the genus *Saccharomyces*, in particular belonging to the species *Saccharomyces cerevisiae* are most preferred.

Examples of suitable bacterial microorganisms are lactic acid bacteria, e.g. *Lactobacillus*.

The microorganism used in the process of the invention may be prepared by any suitable fermentation process known in the art. The microbial biomass may be concentrated prior to its use in the present process, for example by centrifugation or filtration. For example, cream yeast (baker's yeast which has been concentrated to a dry matter content of 15-27% w/w) may be used. Optionally fermentation broths comprising Brewer's yeast or residue yeast derived from breweries (spent Brewer's yeast) may be used.

The present invention provides a process which is especially suitable for large scale production of compositions containing 5'-ribonucleotides. Large scale means that fermentation is performed in fermentors of more than 10 m³.

The autolytic process is initiated by damaging and/or partially disrupting the microbial cell walls. This way the cells are partially opened and at least some of the cell content is released. In order to damage and/or partially disrupt the microbial cell walls, the cells are treated chemically, mechanically or enzymatically using methods known to those skilled in the art.

Mechanical treatments include homogenisation techniques. At this purpose, use of high-pressure homogenisers is possible. Other homogenisation techniques may include mixing with particles, e.g. sand and/or glass beads, or the use of a milling apparatus (e.g. a bead mill).

Chemical treatments include the use of salts, alkali and/or one or more surfactants or detergents. Chemical treatments are less preferred because they may lead to partial degradation of RNA especially when alkali is used, with consequent formation of 2'-ribonucleotides and 3'-ribonucleotides.

The inventors have surprisingly found that the amount of 5'-ribonucleotides in the composition produced by the process of the invention may be high, e.g. higher than when the pH in step b) is 5.1 or higher which is very desirable. In contrast, the pH during the solid/liquid separation step in the process of WO2005067734 is always 5.1. WO2005067734 does not suggest that when the solid-liquid separation and/or the recovering of the RNA-containing cell walls may result in an increased amount of 5'-ribonucleotides.

In an embodiment, the pH during the solid/liquid separation in step b) is lower than 5.1, preferably 4.5 or less, more preferably 4.2 or less, even more preferably 4.0 or less, most preferably 3.5 or less 1 and higher than 1.0. Preferred pH-ranges are from 1.0-5.0 or from 1.0-4.5 or from 1.0-4.2 or from 1.0-3.5 and from 2.0-5.1 or from 2.0-4.5 or from 2.0-4.2. Most preferred is the pH range 2.0-3.5.

The solid-liquid separation in step b) is preferably done by common solid-liquid separation methods, preferably by centrifugation or filtration.

In a preferred embodiment the solid-liquid separation in step b) is done by centrifugation. Use of centrifugation is economically advantageous, in particular when the process is performed at large scale.

In the process of the invention the conditions used in the autolytic process are such that a substantial part of the RNA remains in a form degradable into 5'-ribonucleotides. In this context, with "substantial part of the RNA" is meant preferably at least 50%, more preferably at least 60%, 70%, 75%, even more preferably at least 80%, most preferably at least 83%, al based on the total amount of RNA prior to step b). Thus, the RNA does not need to remain fully intact during the autolytic process, but at least a substantial part of the RNA should remain in a form degradable into 5'-ribonucleotides. Generally up to 100% of the RNA may remain in a form degradable into 5'-ribonucleotides. In a form degradable into 5'-ribonucleotides means that the RNA should be in a form that allows conversion into 5'-ribonucleotides by a suitable enzyme. Preferably the suitable enzyme is a 5'-phosphodiesterase (5'-Fdase).

A form of RNA degradable into 5'-ribonucleotides comprises oligonucleotides containing at least two ribonucleotide units. Therefore RNA in a form degradable into 5'-ribonucleotides may consist of a mixture comprising intact RNA and oligonucleotides or polynucleotides of different lengths. In the context of the present invention an oligonucleotide comprises 2-10 ribonucleotide units, while a polynucleotide comprises more than 10 ribonucleotide units.

The percentage of RNA which remains in a form degradable into 5'-ribonucleotides during the autolytic process is defined as the ratio (×100) between a) the weight percentage of 5'-GMP (calculated as the disodium heptahydrate thereof and based on sodium chloride free dry matter) measured in the autolysate after inactivation of the enzymes participating in the autolysis and conversion of RNA into 5'-ribonucleotides, and b) the weight percentage of GMP (calculated as the disodium heptahydrate thereof and based on sodium chloride free dry matter) measured in the starting material after complete alkaline hydrolysis of RNA. The weight percentage of GMP (calculated as the disodium heptahydrate thereof and based on sodium chloride free dry matter) measured in the starting material after alkaline hydrolysis can be determined from the corresponding weight percentage of free GMP (based on sodium chloride free dry matter) by multiplying the latter with a factor 1.47. The method to determine the amount of 5'-GMP in the autolysate and of GMP after basic hydrolysis is described in Example 1. The method used to determine the amount of 5'-GMP can also be used to determine the amount of 5'-IMP, 5'-AMP, 5'-CMP and 5'-UMP if necessary with some modifications well within the knowledge of those skilled in the art.

The conditions applied in the autolysis to ensure that a substantial part of the RNA remains in a form degradable into 5-ribonucleotides will be generally dependent on the microorganism used.

Preferably damaging and/or partially disrupting the microbial cell wall is done enzymatically because a better control of the process can thereby be achieved and because this method is especially suitable to be used at large scale. Several enzyme preparations can be used like cellulases, glucanases, hemicellulases, chitinases, proteases and/or pectinases. Preferably protease is used, more preferably endoprotease is used. The conditions used to initiate the autolytic process are dependent on the type of enzyme used and can be easily determined by those skilled in the art. Generally the conditions used to enzymatically damage and/or disrupt the microbial cell wall will correspond to those applied during the autolysis of the microorganism.

The autolysis of the microorganism is at least partially effected by active native microbial enzymes released in solution after (partially) damaging and/or disrupting the microbial cell wall wherein the chemicals, or more preferably, the enzymes added to damage and/or to disrupt the microbial cell wall may contribute to the degradation of the microbial cells and of polymeric microbial material.

In particular the first phase of autolysis is performed at a particular pH range combined with a particular temperature.

For instance, the conditions applied in the autolysis of *Saccharomyces cerevisiae* to ensure that a substantial part of the RNA remains in a form degradable into 5'-ribonucleotides are such that the pH in the first phase of the autolysis is between 4.5-9 and/or the temperature is between 50-65° C. Preferably the first 8 hours of the autolysis, more preferably the first 4 hours of the autolysis, are performed at a pH of 4.5-5.5 and at a temperature of 57-65° C., or at a pH 5.5-9 and a temperature of 50-65° C.

The autolysis conditions to be kept after the first phase are less critical. After the first phase the pH is generally kept between 4 and 10 and the temperature is generally kept between 40° C. and 70° C. In general the duration of the autolytic process including the first phase is at most 24 hours.

The present invention may encompass as well a process wherein in step a) a microorganism is subjected to hydrolysis under conditions at which a substantial part of the RNA remains in a form degradable into 5'-ribonucleotides. In the context of the present invention "hydrolysis of a microorganism" is defined as a process wherein the native microbial enzymes have been inactivated and wherein suitable exogenous enzymes added to the microbial biomass to effect degradation of the microbial cells and of the polymeric microbial material.

After autolysis a suspension (autolysate) is obtained which comprises a microbial cell wall fraction, RNA which is for a substantial part in a form degradable into 5'-ribonucleotides, and soluble cell components (e.g. proteins, peptides, amino acids, carbohydrates, etceteras). The cell wall fraction comprises insoluble cell residues, in particular cell walls or fragments thereof.

At the end of the autolytic process and prior to step b), the chemicals used for damaging and/or partially disrupting the microbial cell walls and/or the enzymes which took part in the autolytic process should preferably be neutralised and/or inactivated. The enzymes which took part in the autolysis are the native microbial enzymes and optionally any added exogenous enzyme used to initiate the autolytic process. Neutralisation and/or inactivation of the chemicals and/or the enzymes should occur under conditions at which a substantial part of the RNA remains in a form degradable into 5'-ribonucleotides. Inactivation of the enzymes which took part in the autolysis can be done by pH treatment or preferably by a heat treatment whereby the enzymes are inactivated, a substantial part of the RNA remains in a form degradable into 5'-ribonucleotides. The enzymes can be inactivated by heat treatment, for instance by heating the mixture from 5 minutes to 1 hour at a temperature from 65° C. to 95° C., more preferably by heating from 30 minutes to 1 hour at a temperature from 65° C. to 75° C., wherein typically a shorter reaction time may be used at higher reaction temperatures. For example, heating the mixture for 1 hour at 65° C., or for 30 minutes at 75° C. may be sufficient to inactivate the enzymes whereby a substantial part of the RNA remains in a form degradable into 5'-ribonucleotides.

In step b) of the process of the invention the autolysate is subjected to solid/liquid separation and the RNA-containing cell wall fraction is recovered, wherein the pH during this is lower than 5.1, preferably 4.5 or less, more preferably 4.2 or less, even more preferably 4.0 or less, most preferably 3.5 or less 1 and higher than 1.0. Preferred pH-ranges are from 1.0-5.0 or from 1.0-4.5 or from 1.0-4.2 or from 1.0-3.5 and from 2.0-5.1 or from 2.0-4.5 or from 2.0-4.2. Most preferred is the pH range 2.0-3.5.

The inventors have surprisingly found that a substantial part of the total RNA remains associated with the recovered cell wall fraction obtained after step b) of the process of the invention. In an embodiment, in step b) at least 55%, more preferably at least 75%, most preferably at least 90% of the total RNA remains associated with the cell wall fraction. Example 2 demonstrates that up to 94.7% of the total RNA in the autolysate remains associated with the cell wall fraction. It is also demonstrated in Example 2 that the percentage RNA bound to the yeast cell walls and the turbidity of the yeast extract are a function of the pH during the solid/liquid separation: at lower pH values, more RNA remains bound to the cell walls and the turbidity of the yeast extract is decreasing.

The total amount of RNA (i.e. prior to step b) can be determined by analyzing the autolysate obtained in step a). A method to analyze RNA is described in Example 1.

The percentage of the RNA which remains associated with the cell wall fraction is defined as the ratio (×100) between a) the amount of RNA in grams in the cell wall fraction of an autolysate originating from a fixed amount of starting material, and b) the amount of RNA in grams present in the same fixed amount of starting material. The method to determine the amount of RNA in the cell wall fraction and in the starting material is described in example 1. Preferably the starting material may be the autolysate obtained after step a) of the process of the invention.

In order to increase the amount of recovered RNA in a form degradable into 5'-ribonucleotides, the autolysate may be subjected to ultra filtration (UF) instead of to a common solid-liquid separation method like centrifugation or filtration. In this way, a mixture of the RNA-containing cell wall fraction and RNA derived from the microbial soluble fraction is recovered. Thus, not only the RNA associated with the cell wall fraction is separated from the microbial soluble fraction but also the RNA which had been released into solution during autolysis. In cases where UF is used to recover RNA, preferably membranes with a molecular weight cut off from 10 to 50 kDa or preferably from 20 to 50 kDa can be used. In general a larger molecular weight cut off allows a higher flow rate through the membrane, but might result in larger losses and/or less pure products. The type of solid-liquid separation used and the efficiency of said solid-liquid separation can influence, among other factors, the amount of 5'-ribonucleotides obtained in the compositions of the invention.

In step b) the RNA-containing cell wall fraction is recovered and the liquid fraction may be discarded. However, in the process of the invention it is also possible to recover both the RNA containing cell wall fraction as well as the liquid fraction. Said liquid fraction may actually be a yeast extract. Not only is this a very economical, but said yeast extract obtainable by the process of the invention by recovering the liquid fraction in step b) may be characterized in that it has a low turbidity, which makes it very suitable to be used in those applications where clarity is important, such as clear soups and drinks.

In step c) the RNA in the recovered cell wall fraction is converted into 5'-ribonucleotides. This is preferably done by enzymatically treating the RNA-containing cell wall fraction, optionally mixed with RNA derived from the microbial soluble fraction obtained by ultrafiltration.

5'-Phosphodiesterase (5'-Fdase) is preferably used to convert RNA into 5'-ribonucleotides. 5'-phosphodiesterase can be obtained from a microbial or a vegetable source (for example a malt root extract). An example of a commercially available microbial 5'-Fdase is Enzyme RP-1 produced by Amano (Japan).

Optionally, 5'-AMP is converted to 5'-IMP by a deaminase, for example adenyl deaminase. An example of a commercially available deaminase is Deaminase 500 produced by Amano (Japan).

Treatment of RNA by 5'-Fdase and deaminase can be performed in a two-step or in a single step process.

In a preferred embodiment, the process of the invention comprises after step c)

d) subjecting the 5'-ribonucleotides to a solid-liquid fractionation and recovering the 5'-ribonucleotides, preferably by separating the 5'-ribonucleotides from the cell wall fraction, for instance by centrifugation or filtration or by any other method suitable to achieve solid/liquid separation. This allows to obtain a composition having a very high amount of 5'-ribonucleotides, e.g. up to 90% w/w, 95% w/w, or even 98% w/w or 99% w/w, all based on total dry matter.

In an embodiment, the 5'-ribonucleotides are purified by separating said 5'-ribonucleotides from components having a higher molecular weight than the 5'-ribonucleotides by ultrafiltration. The degree of purification will depend on the molecular weight cut-off of the ultrafiltration membrane used. For instance, ultrafiltration membranes as mentioned above can be used.

It will be understood that in the context of the present invention a wording like "recovering the RNA" or "converting the RNA" does not necessarily mean that all RNA is recovered or converted, respectively. It will be clear to those skilled in the art that the amount of the RNA which is recovered will depend on the type of separation method used. It will also be clear that the amount of RNA which is converted will depend on several factors, one of which is the accessibility of the RNA associated with the cell wall insoluble fraction to the enzymes used in this step.

The process of the invention has several benefits. It allows for the production of a very pure 5'-ribonucleotides composition. Because it may comprise only 2 steps, it is very simple. In addition, it may also allow for the production of a yeast extract having a low turbidity. In this way, both a very clear yeast extract may be produced in addition to a cell wall fraction rich in RNA and/or a cell wall fraction rich in 5'-ribonucleotides and/or a very pure 5'-ribonucleotides fraction.

The invention will now be illustrated by some examples which however do not intend to be limiting.

EXAMPLES

Example 1

Preparation of a Composition Comprising 5'-Ribonucleotides

Two liters of cream yeast from *Saccharomyces cerevisiae* were heated to 60° C. Subsequently 0.5 ml Alcalase (commercially available serine protease from Novozymes, Denmark) was added and the mixture was incubated for 4 hours at pH 6.0 and 60° C. The conditions were adjusted to pH 5.1 and 51.5° C. and an additional 2 ml of Alcalase was added to the reaction mixture. The mixture was incubated for 20 hours at pH 5.1, 51.5° C. Next, the mixture or autolysate was heated for 1 hour at 65° C. to inactivate all enzyme activity.

The RNA content of the autolysate was 8.7% w/w based on total dry matter. One part of the autolysate was treated with 5'-phosphodiesterase which resulted in an amount of 5'-GMP of 2.65% w/w, expressed as disodium heptahydrate and based on sodium chloride free dry matter. It follows that the fraction of RNA which was degradable into 5'-ribonucleotides was 83% (w/w).

The other part of the autolysate was subjected to a first solid/liquid separation by way of centrifugation at a pH of either 5.1 (comparative experiment), 4.2 (experiment 1), or 3.5 (experiment 2). The cell wall fractions were collected without further pH adjustment and washed two times with water and analyzed for RNA content. The clear extract (as the supernatant) was adjusted to a dry matter content of either 13% or 2.5% by adding water and was subsequently analyzed for turbidity.

The cell wall fractions were further treated 5'-phosphodiesterase at a temperature of 65° C. and a pH of 5.3. Next, 5'-AMP was converted by the enzyme deaminase into 5'-IMP at a temperature of 55° C. and at pH 5.1. After both the 5'-phosphodiesterase and the deaminase treatment the cell wall fraction was subjected to a second solid/liquid separation by means of centrifugation and the clear fraction was analysed for 5'-ribonucleotide content.

Some samples were also incubated with 5'-Fdase in order to establish whether the RNA present in the samples could be converted into 5'-ribonucleotides (i.e. whether the RNA was in a form degradable into 5'-ribonucleotides by e.g. 5'-Fdase) and some of these samples were also treated with deaminase to convert the 5'-AMP into 5'-IMP. The amount of 5'-GMP, 5'-AMP and 5'-IMP in the samples (expressed as weight percentage of the disodium heptahydrate thereof based on sodium chloride free dry matter) were subsequently determined by means of HPLC according to the following method. 5'-GMP, 5'-AMP and 5'-IMP in yeast extracts were quantified by HPLC using a Whatman Partisil 10-SAX column, a phosphate buffer pH 3.35 as eluent and UV detection. Concentrations were calculated on basis of 5'-GMP, 5'-IMP and 5'-AMP standards. Sodium chloride was determined by measuring the chloride ions in the sample with a Jenway chloride meter PCLM 3 (Jenway, Essex, England) and calculating the corresponding amount of sodium chloride.

TABLE 1

Results of Example 1

|  | Comparative Example A | Experiment 1 | Experiment 2 |
|---|---|---|---|
| pH during the first solid/liquid separation | 5.1 | 4.2 | 3.5 |
| RNA content of the cell wall fraction (% w/w based on dry matter) | 15.2 | 16.7 | 19.9 |
| 5'-GMP content (% w/w) after the phosphodiesterase treatment and before the second solid/liquid separation | 5.3 | 5.7 | 6.6 |
| % of the RNA in the cell wall fraction | 55 | 75 | 90 |
| 5'-GMP content in the clear fraction (% w/w) obtained after the second solid/liquid separation (5'-phosphodiesterase treatment only) | 18.6 | 22.4 | 25.5 |
| 5'-GMP content in the clear fraction (% w/w) obtained after the second solid/liquid separation (5'-phosphodiesterase and subsequent deaminase treatment) | 19.6 | 22.7 | 24.9 |
| 5'-IMP content in the clear fraction (% w/w) obtained after the second solid/liquid separation (5'-phosphodiesterase and subsequent deaminase treatment) | 20.2 | 23.1 | 25.3 |
| Turbidity of the clear extract obtained after the first solid/liquid separation (NTU at 13% dry matter) | 298 | 49 | 31 |
| Turbidity of the clear extract obtained after the first solid/liquid separation (NTU at 2.5% dry matter) | 57 | 9.4 | 6.0 |

RNA was analyzed as follows: RNA was hydrolysed during an alkaline treatment. GMP (i.e. 2'-GMP and 3'-GMP derived from the hydrolysis of RNA) was quantified by means of HPLC, using 5'-GMP as a standard, using a Whatman Partisil 10-SAX column, a phosphate buffer at pH 3.35 as eluent and UV detection. The weight percentage of RNA content based on sodium chloride free dry matter corresponds to ~4 times the weight percentage of free GMP based on sodium chloride free dry matter.

NTU (turbidity) was determined by nephelometry with a HACH 2100 N turbidity meter (Hach-Lange, Dusseldorf, Germany) equipped with a tungsten lamp (400-600 nm) at a temperature of 20° C.

NTU means Nephelometric Turbidity Unit and is measured with the HACH 2100 N turbidity meter. The method is based on light scattering while measuring the scattered light at an angle of 90° and using formazin solutions as a standard.

Example 2

RNA-Partitioning over Cell Walls and Supernatant as a Function of pH

The experiments of Example 1 were repeated at pH values ranging from 2.0 to 5.01. All conditions were identical except that the clear extract (the supernatant) was adjusted to a dry matter content of 5% by adding water before being analyzed for turbidity. Also, RNA in the cell wall fractions was not digested by 5'-Fdase.

TABLE 2

Results of Example 2

| | Experiment 3 | Experiment 4 | Experiment 5 | Experiment 6 | Experiment 7 | Experiment 8 | Experiment 9 | Experiment 10 |
|---|---|---|---|---|---|---|---|---|
| pH during the first solid/liquid separation | 2.01 | 2.49 | 2.90 | 3.29 | 3.49 | 3.99 | 4.50 | 5.01 |
| % of the RNA in the cell wall fraction* | 94.6 | 94.7 | 94.1 | 89.4 | 79.8 | 59.5 | 55.3 | 53.8 |
| % of the RNA in the supernatant* | 5.4 | 5.3 | 5.9 | 10.6 | 20.2 | 40.5 | 44.7 | 46.2 |
| Turbidity of the supernatant (NTU at 5% dry matter) | 6.0 | 5.3 | 6.1 | 3.8 | 6.0 | 19.2 | 34.8 | 32.9 |

*the sum of the RNA in the cell walls and the supernatant is 100% by definition

The invention claimed is:

1. A process for producing a composition comprising 5'-ribonucleotides, said process comprising:

a) subjecting a microorganism to autolysis under conditions at which at least 50% of the RNA remains in a form degradable into 5'-ribonucleotides;

b) subjecting the autolysate from a) to solid/liquid separation and recovering an RNA-containing cell wall fraction; and c) converting RNA in the recovered RNA-containing cell wall fraction into 5'-ribonucleotides, wherein the solid/liquid separation in b) is done at a pH of lower than 4.0 and higher than 1.0, and wherein at least 75% of the RNA remains associated with the RNA-containing cell wall fraction obtained in b).

2. The process according to claim 1, wherein the pH in b) is 3.5 or less and higher than 1.0.

3. The process according to claim 1, wherein the pH is higher than 2.0.

4. The process according to claim 1, wherein the recovering in b) is done by centrifugation.

5. The process according to claim 1, further comprising after step c):

d) subjecting the 5'-ribonucleotides to a solid-liquid fractionation and recovering 5'-ribonucleotides.

* * * * *